(12) United States Patent
Bulaj et al.

(10) Patent No.: US 9,569,562 B2
(45) Date of Patent: Feb. 14, 2017

(54) DISEASE THERAPY GAME TECHNOLOGY

(75) Inventors: Grzegorz Wlodzimierz Bulaj, Salt Lake City, UT (US); Carol S. Bruggers, Salt Lake City, UT (US); Roger Alan Altizer, Jr., Salt Lake City, UT (US); Robert R. Kessler, Salt Lake City, UT (US); Craig Bernreuter Caldwell, Salt Lake City, UT (US); Wade Ray Patterson, Salt Lake City, UT (US); Kurt Joseph Coppersmith, West Point, UT (US); Laura Mae Warner, Salt Lake City, UT (US); Brandon H. Davies, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 331 days.

(21) Appl. No.: 13/475,740

(22) Filed: May 18, 2012

(65) Prior Publication Data

US 2013/0131846 A1    May 23, 2013

Related U.S. Application Data

(60) Provisional application No. 61/488,358, filed on May 20, 2011.

(51) Int. Cl.
| | | |
|---|---|---|
| *G06F 17/00* | (2006.01) | |
| *G06F 19/00* | (2011.01) | |
| *G06F 17/40* | (2006.01) | |

(52) U.S. Cl.
CPC ........... *G06F 17/40* (2013.01); *G06F 19/3481* (2013.01)

(58) Field of Classification Search
CPC ..... G06F 3/011; G06F 3/04815; A63F 13/212
USPC ........................................... 463/12
See application file for complete search history.

(56) References Cited

U.S. PATENT DOCUMENTS

| | | | |
|---|---|---|---|
| 5,918,603 A | 7/1999 | Brown | |
| 8,425,382 B2 * | 4/2013 | Bennett, II | 482/8 |
| 2004/0063083 A1 * | 4/2004 | Rink | 434/247 |
| 2008/0243038 A1 * | 10/2008 | Bennett | 601/33 |

OTHER PUBLICATIONS

Debra A. Lieberman, et al.,—"The Power of Play" 123:2507-2516—Circulation Journal of the American Heart Association—Published Apr. 25, 2011—Baltimore, Maryland—11 pages.

(Continued)

*Primary Examiner* — Reginald Renwick
(74) *Attorney, Agent, or Firm* — Workman Nydegger

(57) ABSTRACT

A video game in possession of and/or in the proximity of a patient. The patient computing system receives an indication that it is to begin a game, and executes the game using identified game parameters that are associated with the patient by a clinician as part of a disease therapy program. As the game executes, game state progresses in response to physical activity of the patient, causing the patient to exercise. The physical activity is received as input into the patient computing system. Such input causes game state to be progressed dependent on the identified game parameters that are associated with the game. Thus, the game is tailored for the patient by a clinician in order to motivate physical activity that is medically beneficial to the patient in order to advance through the disease therapy program.

24 Claims, 9 Drawing Sheets

(56) References Cited

OTHER PUBLICATIONS

Marina Papastergiou—"Exploring the potential of computer and video games for health and physical education": A literature review—published on Apr. 1, 2009—Elsevier Computers & Education 53 (2009) 603-622—Trikala, Greece—20 pages.

* cited by examiner

DISEASE THERAPY GAME TECHNOLOGY

CROSS-REFERENCE TO RELATED APPLICATIONS

This application claims the benefit under 35 U.S.C. 119(e) of U.S. Provisional Application No. 61/488,358 filed May 20, 2011, which provisional patent application is herein incorporated by reference in its entirety.

BACKGROUND

Chronic diseases often lead to depression, withdrawal, mood disturbances, diminished quality of life and a weakening of the "fighting spirit" in a patient. Such co-morbidities often further compromise overall health, affecting medical treatments and escalating care costs for chronic diseases. Current interventions employed for these co-morbidities include counseling, physical, and pharmacological therapies. Example diseases include cancer, cystic fibrosis, stroke, epilepsy, neuropathic pain, Parkinson's disease, or multiple sclerosis. As an example, the prevalence of depression in cancer patients alone is over 10%.

The depression is combined with the physical de-conditioning and generalized weakness that results from the physical effects of the disease, and possibly the therapy used to treat the disease. Hospitalization may also lead to a diminished physical strength that can affect the body's innate ability to fight a disease. Although physical exercise is known to improve the immune system response, patients lacking a motivation to exercise in a consistent manner may compromise their body's innate ability to fight the disease.

Health-promoting interactive technologies provide opportunities for patient self-education, with the goal of improving patient understanding of symptoms and medications, which in turn promotes improved patient disease management. Currently, there are two major categories of health-related interactive games: sedentary and activity-promoting video games.

Sedentary video games, such as Packy & Malone and Re-Mission, focus on educating patients regarding a specific health condition by merging lessons and quizzes with puzzles and plots. In Packy & Malone, a diabetic patient learns to manage his/her diabetes by maintaining the protagonist's blood sugar within a healthy range through proper insulin use and diet, while playing towards the ultimate goal of saving a summer camp from the destruction of rodents. Re-Mission, introduced in 2006 by HopeLab, was designed to empower cancer patients by manipulating an on-screen microscopic robot to destroy cancer cells, while simultaneously educating patients about cancer and management of chemotherapy-related side effects. Two randomized, multicenter trials have demonstrated efficacy of Re-Mission in educating cancer patients and in improving adherence to chemotherapy treatments.

Commercially available activity-promoting video games, or "exergames," that employ gaming console systems such as Wii, XBOX or PlayStation, have been utilized for clinical purposes. For example, while "Dance Dance Revolution" was not designed specifically to treat childhood obesity, it is an effective aerobic workout that promotes weight loss in childhood obesity. Similarly, Wii Boxing and Bowling have been effective in neuro-rehabilitation of adults with cerebral palsy and stroke. Therapeutic applications of existing video games were recently reviewed. However, activity-promoting interactive video games that are "customized" for patients with specific diseases have not yet been reported.

BRIEF SUMMARY

At least one embodiment described herein relates to a method for operating a patient computing system, such as a game device, accessible to a patient (also referred to as a "patient computing system"). The patient computing system receives an indication that it is to begin a game. Such a request may come from, for example, the patient, or perhaps from a clinician. A clinician is defined herein as any medical staff that is assisting the patient in a disease therapy program. Examples of such medical staff including doctors, nurses, physical therapists, and so forth.

Before, during, or after the patient computing system initiates the game, the patient computing system identifies game parameters that are associated with the patient and that are created due to action by a clinician as part of a disease therapy program. In any case, the game is executed using the identified game parameters that are associated with the game. As the game executes, game state progresses in response to physical activity of the patient, incentivizing the patient to exercise. The physical activity is received as input into the patient computing system. Such input causes game state to be progressed dependent on the identified game parameters that are associated with the game. Thus, the game is tailored for the patient by a clinician in order to motivate physical activity that is medically beneficial to the patient in order to advance through the disease therapy program.

In accordance with at least one embodiment described herein, the resulting input generated from the patient's physical activity is stored for evaluation of a clinician. In some embodiments, the clinician may have a separate computing system (i.e., a "clinical computing system") that is capable of communication with the patient communication so as to receive a representation of at least a portion of this input, so that the clinician can evaluate the physical activity of the patient without necessarily being present. In some embodiments, the clinician may use this or another clinical computing system to modify the patient game parameters. Such modifications may be made based on the clinician's judgment regarding changes that should be made to properly motivate patient physical activity that is best suited to advance through the disease therapy program. Such clinician judgment may be based at least in part upon the evaluation of the game input previously received by the patient computing system.

This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features can be obtained, a more particular description of various embodiments will be rendered by reference to the appended drawings. Understanding that these drawings depict only sample embodiments and are not therefore to be considered to be limiting of the scope of the invention, the embodiments will be described and explained with additional specificity and detail through the use of the accompanying drawings in which.

DETAILED DESCRIPTION

In accordance with embodiments described herein, a video game is accessible to a patient in the form of a patient computing system. The patient computing system receives an indication that it is to begin a game, and executes the game using identified game parameters that are associated with the patient by a clinician as part of a disease therapy program. As the game executes, game state progresses in response to physical activity of the patient, causing the patient to exercise. The physical activity is received as input into the patient computing system. Such input causes game state to be progressed dependent on the identified game parameters that are associated with the game. Thus, the game is tailored for the patient by a clinician in order to motivate physical activity that is medically beneficial to the patient in order to advance through the disease therapy program. First, some introductory discussion regarding computing systems will be described with respect to FIG. 1. Then, embodiments of the disease therapy game system will be described with respect to FIGS. 2 through 7.

Computing systems are now increasingly taking a wide variety of forms. Computing systems may, for example, be handheld devices, appliances, laptop computers, desktop computers, mainframes, distributed computing systems, or even devices that have not conventionally been considered a computing system. In this description and in the claims, the term "computing system" is defined broadly as including any device or system (or combination thereof) that includes at least one physical and tangible processor, and a physical and tangible memory capable of having thereon computer-executable instructions that may be executed by the processor. The memory may take any form and may depend on the nature and form of the computing system. A computing system may be distributed over a network environment and may include multiple constituent computing systems.

Figure 1:
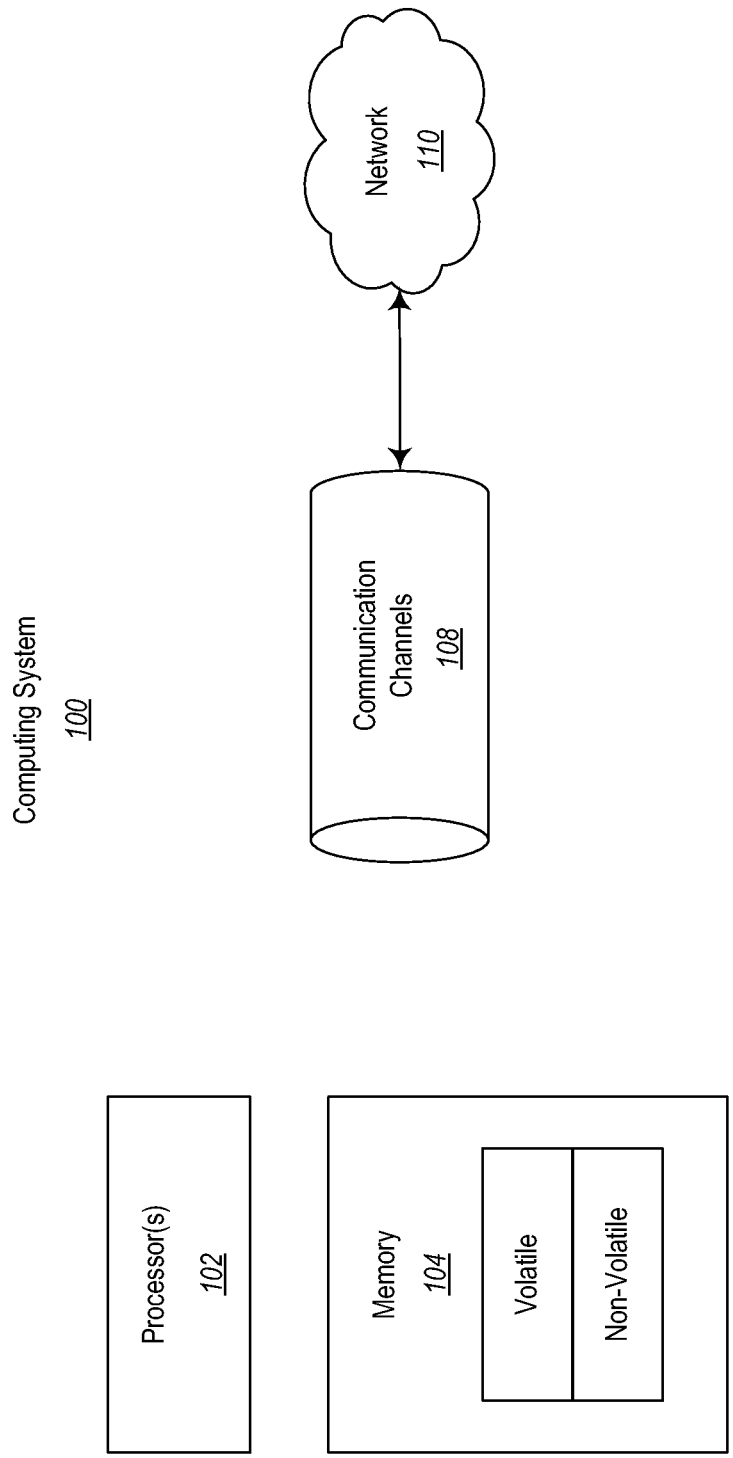
FIG. 1 illustrates a computing system in which some embodiments described herein may be employed.

As illustrated in FIG. 1, in its most basic configuration, a computing system 100 typically includes at least one processing unit 102 and memory 104. The memory 104 may be physical system memory, which may be volatile, non-volatile, or some combination of the two. The term "memory" may also be used herein to refer to non-volatile mass storage such as physical storage media. If the computing system is distributed, the processing, memory and/or storage capability may be distributed as well. As used herein, the term "module" or "component" can refer to software objects or routines that execute on the computing system. The different components, modules, engines, and services described herein may be implemented as objects or processes that execute on the computing system (e.g., as separate threads).

In the description that follows, embodiments are described with reference to acts that are performed by one or more computing systems. If such acts are implemented in software, one or more processors of the associated computing system that performs the act direct the operation of the computing system in response to having executed computer-executable instructions. An example of such an operation involves the manipulation of data. The computer-executable instructions (and the manipulated data) may be stored in the memory 104 of the computing system 100. Computing system 100 may also contain communication channels 108 that allow the computing system 100 to communicate with other computing systems over, for example, network 110.

Embodiments described herein may comprise or utilize a special purpose or general-purpose computer including computer hardware, such as, for example, one or more processors and system memory, as discussed in greater detail below. Embodiments described herein also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: computer storage media and transmission media.

Computer storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

As an example, the computing system may be implemented in a cloud computing environment. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

For instance, cloud computing is currently employed in the marketplace so as to offer ubiquitous and convenient on-demand access to the shared pool of configurable computing resources. Furthermore, the shared pool of configurable computing resources can be rapidly provisioned via virtualization and released with low management effort or service provider interaction, and then scaled accordingly.

A cloud computing model can be composed of various characteristics such as on-demand self-service, broad network access, resource pooling, rapid elasticity, measured service, and so forth. A cloud computing model may also come in the form of various service models such as, for example, Software as a Service ("SaaS"), Platform as a Service ("PaaS"), and Infrastructure as a Service ("IaaS"). The cloud computing model may also be deployed using different deployment models such as private cloud, community cloud, public cloud, hybrid cloud, and so forth. In this description and in the claims, a "cloud computing environment" is an environment in which cloud computing is employed.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Figure 2:
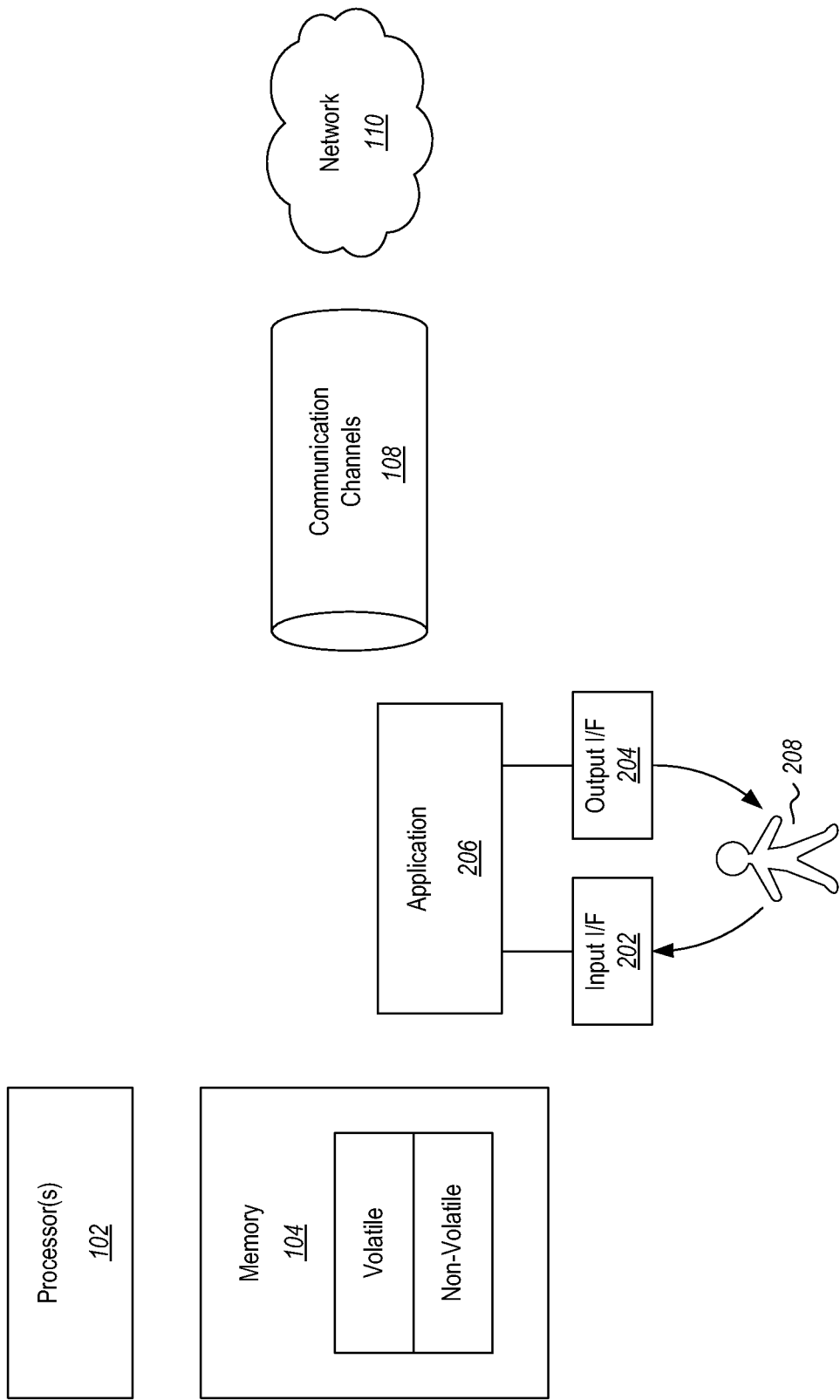
FIG. 2 illustrates a more specific example of the computing system of FIG. 1, which is more adapted to interface with a user.

While FIG. 1 illustrates the fundamental components of a computing system 100, FIG. 2 illustrates a computing system 200 that is more adapted to interface with a user, and in addition to the general components of FIG. 1, also includes an input interface 202 and an output interface 204. The computing system 200 also has an application 206 running thereon. The application 206 is an example of the computer-executable instructions referred to above. For instance, in a disease therapy system such as the system described below with respect to FIG. 3, there might be a patient computing system that interfaces with the patient, and a clinician computing system that interfaces with a clinician (e.g., a doctor, nurse, medical assistant, or other medical worker) that is charged with assisting the patient in the disease therapy program. Each of the patient computing systems and the clinician computing systems may be structured as described for the computing system 200 of FIG. 2. In that case, the application 206 may be a distributed disease therapy application with a component of the application on the patient computing system, and a component of the application on the clinician computing system.

Input interface 202 provides an interface for receiving information from the user 208 (e.g., the patient in the case of a patient computing system or a clinician in the case of a clinician computing system) for entry into the computing system 200. The computing system 200 may have one or more input interfaces that use the same or a different input interface technology. Input interface 202 may provide an interface to receive input from various input technologies including, but not limited to, keyboard, a pen and touch screen, mouse, a track ball, a touch screen, a keypad, a button, a joystick, game control (e.g., of any type including, as examples, a nunchuck, a balance board controller), motion sensor that may be mounted to a body of a user or a game control, and so forth, to provide information used by computing system 200. The same interface may support both input interface 202 and output interface 204. For example, a display may accept user input and present an output to the user.

Output interface 204 provides an interface for outputting information to a user 208 of the computing system 200 (e.g., a patient in the case of a patient computing system, or a clinician in the case of a clinician computing system). For example, output interface 204 may include an interface to one or more displays, speakers, printers and so forth.

Figure 3:
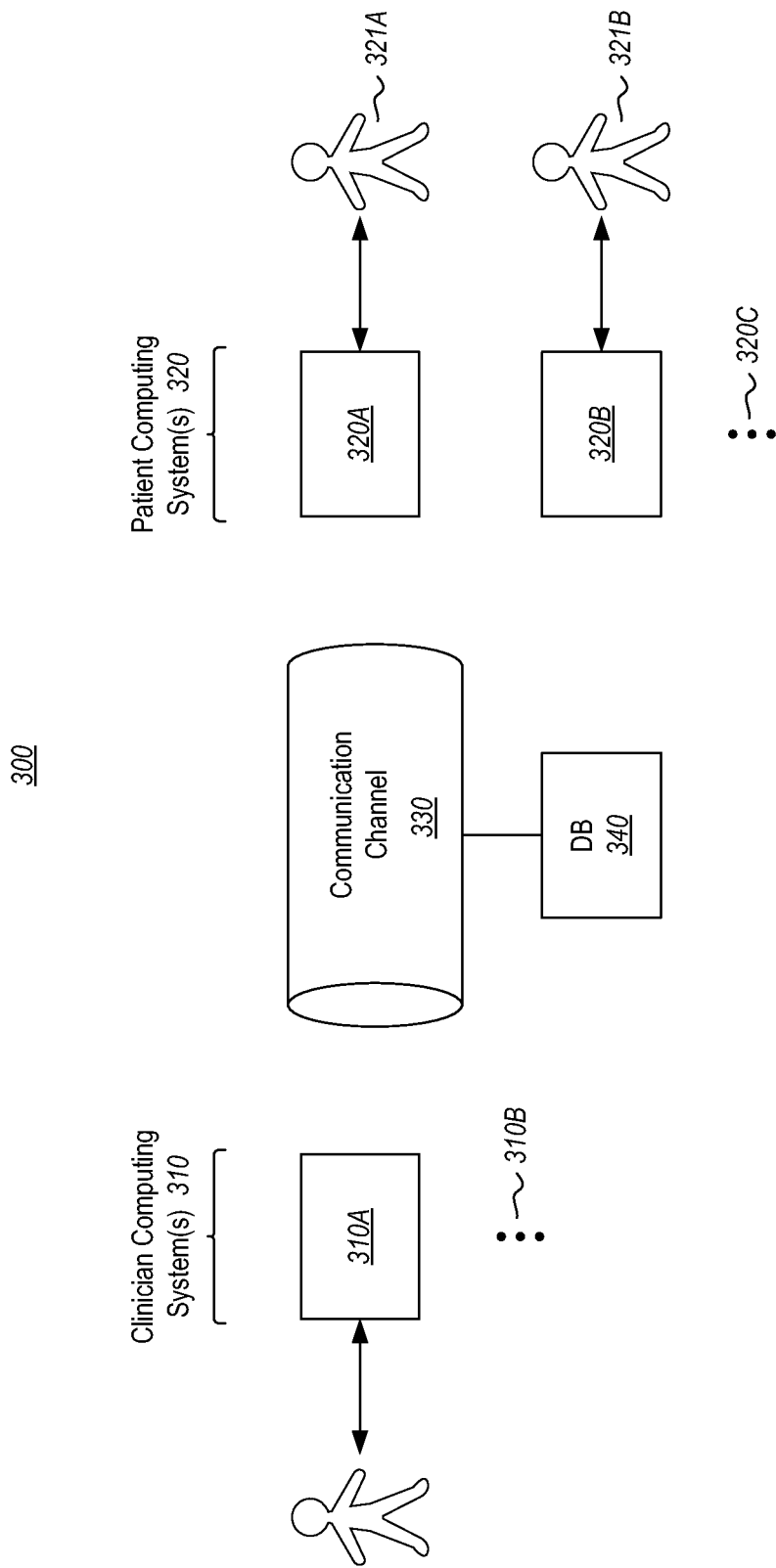
FIG. 3 illustrates a disease therapy system in accordance with the principles described herein, and which includes one or more patient computing systems interfacing with patients, and one or more clinician computing systems interfacing with clinicians.

FIG. 3 illustrates a disease therapy system 300 in accordance with the principles described herein. The disease therapy system 300 includes one or more clinician computing systems 310 including a first clinician computing system 310A with which a clinician 311 may interface. However, the ellipses 310B represents that there may be multiple clinician computing systems that a clinician may interface with as part of the disease therapy system 300. For instance, the same clinician 311 may interface with multiple clinician computing systems, or multiple clinicians may interface with various clinician computing systems within the disease therapy system 300. Multiple clinicians may also interface with a single clinician computing system, such as the clinician computing system 310A. Each of the clinician computing systems may be structured as described above for the computing system 200 of FIG. 2 in which the clinician uses input interface 202 to provide input into the clinician computing system, and in which the clinician uses output interface 204 to receive output from the clinician computing system. Furthermore, the application 206 represents a clinician portion of a distributed disease therapy application.

The disease therapy system 300 also includes patient computing systems 320. For instance, patient 321A interfaces with patient computing system 320A, and patient 321B interfaces with patient computing system 320B. However, the ellipses 320C represents that there may be other numbers of patient computing systems within the disease therapy system, from as few as one, and with no upper limit.

While there might be one dedicated patient computing system for each patient, alternatively, multiple patients might work with a single patient computing system (though while changing the disease therapy program as appropriate for the patient currently working with the patient computing system), and a single patient might work with multiple patient computing systems. For instance, a single patient might interface with patient computing systems in a medical setting (such as a hospital or medical office), or in a non-medical setting (such as work, home, or vacation). Each of the patient computing systems 320 may be structured as described above for the computing system 200 of FIG. 2 in which the patient uses input interface 202 to provide input into the patient computing system, and in which the patient uses output interface 204 to receive output from the clinician computing system. Furthermore, the application 206 represents a patient portion of a distributed disease therapy application. In some embodiments, all or a portion of the patient and/or clinician component of the disease therapy application may reside in a cloud computing environment.

A communication channel 330 interfaces between the clinician computing system(s) 310 and the patent computing system(s) 320. For instance, if each of the clinician and patient computing systems are an embodiment of the computing system 100 of FIG. 1, the communications channel 330 may be enabled by the communication channel 108 of FIG. 1. The communication channel 330 may be, for example, a network as previously defined herein. A database 340 may reside within the communication channel 330, allowing the patient computing system and the clinician computing system to access the database 340. The database 340 might store game parameters for any number of patients, and also store activity results for many patients in response to performing games.

The disease therapy game performs operations associated with an interactive video game used as part of a disease therapy for a patient. Some or all of the operations described herein may be embodied in disease therapy game application 206. The operations may be implemented using hardware, firmware, software, or any combination of these methods. With reference to the example embodiment of FIG. 2, disease therapy game application 206 is implemented in software. Disease therapy game application 206 may be written using one or more programming languages, assembly languages, scripting languages, etc.

Disease therapy game application 206 may be implemented as a Web application that supports a communication protocol. For example, disease therapy game application 206 may be configured to accept hypertext transport protocol (HTTP) requests and to send HTTP responses along with optional additional data content which may include web pages such as hypertext markup language (HTML) documents and linked objects in response to the HTTP requests.

Disease therapy game application 206 further may provide information or data organized in the form of a website accessible over a network. A website may comprise multiple web pages that display a specific set of information and may contain hyperlinks to other web pages with related or additional information. Each web page is identified by a uniform resource locator (URL) that includes the location or address of the computing device that contains the resource to be accessed in addition to the location of the resource on that computing device. The type of file or resource depends on the Internet application protocol. For example, HTTP and HTTP secure (HTTPS) describe a web page to be accessed with a browser application. The file accessed may be a simple text file, an image file, an audio file, a video file, an executable, a common gateway interface application, a Java applet, or any other type of file supported by HTTP. Thus, the patient and/or clinician need not be in close proximity to the respective patient computing systems and clinician computing systems that they access.

In that case, a browser application may perform operations associated with retrieving, presenting, and traversing information resources provided by a web application and/or web server as known to those skilled in the art. An information resource is identified by a uniform resource identifier (URI) and may be a web page, image, video, or other piece of content. Hyperlinks in resources enable users to navigate to related resources. Example browser applications include Navigator by Netscape Communications Corporation, Firefox® by Mozilla Corporation, Opera by Opera Software Corporation, Internet Explorer® by Microsoft Corporation, Safari by Apple Inc., Chrome by Google Inc., and so forth, as known to those skilled in the art.

Figure 4:
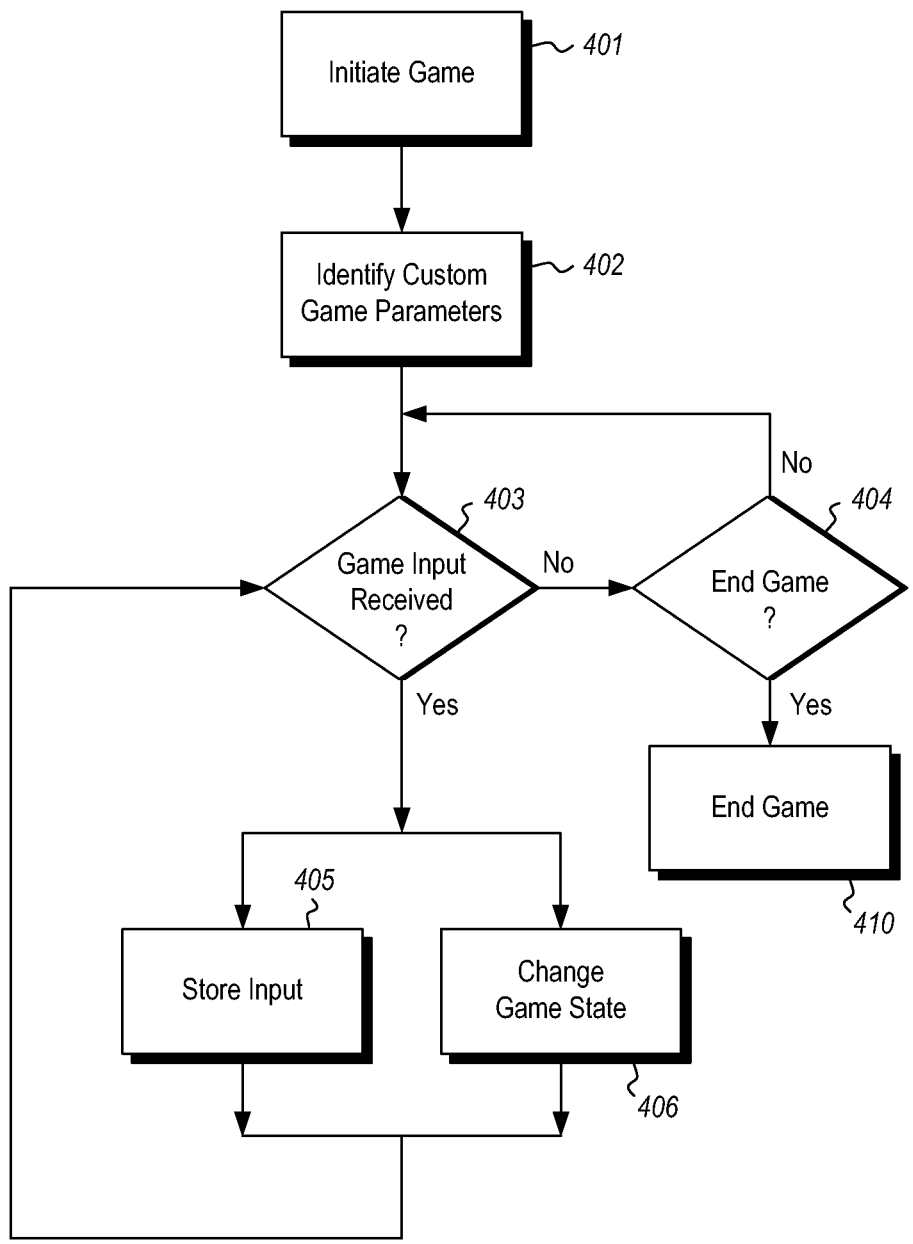
FIG. 4 illustrates a flowchart of a method for operating a patient computing system in advancement of a disease therapy program.

FIG. 4 illustrates a flowchart of a method 400 for operating the patient computing system. The patient computing system detects that it is appropriate to initiate a disease therapy game (act 401). For instance, the patient computing system may receive a request to initiate the disease therapy game from a patient and/or a clinician. Alternatively, the game may be initiated automatically in response to one or more events. For instance, the game may be initiated upon a certain time of day being reached, or perhaps if certain parameters of the patient (heart rate, blood pressure, consciousness state) is within a certain range.

The patient computing system identifies custom game parameters (act 402) that are associated with a patient and that are created due to action of a clinician as part of a disease therapy program. Such game parameters may be set in a manner that considers the personal medical condition of the patient, and provides a good balance of positive motivation to engage in exercise, while recognizing physical limits of the patient. For instance, the clinician might consider whether or not the patient has certain range of motion limitations, the patient's degree of muscle strength in different parts of the body, the psychology of the patient, the cardiovascular health of the patient, the age or gender of the patient, and any other medical consideration that is specific to the patient. The clinician may use the clinician computing system to cause such game parameters to be created as described in further detail below. The clinician may periodically evaluate the patient's condition to cause the game parameters to change if appropriate. Such periodic evaluation might even occur during the game itself.

The clinician may use the clinician computing system to directly define or set the value of a game parameter. For instance, suppose that one game parameter indicates an ideal range of motion for the patient's right arm. The clinician may specific the range of motion directly (e.g., in units of length, by identifying relative position of the beginning and end point, by specifying the relative position of the beginning point of the range of motion with respect to that reference, a relative position of the ending point of the range of motion with respect to that or another reference, by specifying relative positions of one or more intermediary positions in the range of motion, and so forth). The clinician might also directly set game parameters such as ideal patient heart rate or blood pressure, wherein the game is response to measurements to try to maintain close to the ideal specified in the game parameter.

Alternatively or in addition, the game parameters may be defined by a computing module in response to clinician input. For instance, the disease therapy program at the clinician computing system and/or at the patient computing system may calculate the game parameters based on clinician input. For instance, suppose that the clinician enters an age, gender, height, and body mass index for a given patient, the computing module might calculate an appropriate range of motion as a game parameter for the patient. The computing module might also consider dynamically changing conditions measured by the computing module. For instance, the computing system might factor in the time of day, the patient's heart rate, oxygen levels, blood pressure, brain activity, and so forth, in adjusting some game parameters.

After the game begins, the patient computing system may receive input from the user (decision block 403), the input caused by physical activity of the patient. If no input is detected (No in decision block 403), then the game continues (No in decision block 404), until input is received (Yes in decision block 403), or alternatively until the patient computing system ends the game (act 410) in response to its determination that the game should be ended (Yes in decision block 404).

While the game encourages exercise, the game may end even without the patient requesting the game to end. This is designed to prevent over-exercise, and/or game addiction. There may be a cool-down timer that is activated when the input indicates that the physical activity of the patient has exceeded a threshold. Once the cool down timer is activated, the patient cannot engage with the game until the cool down timer expires. Once again, while entertainment of the patient is important in motivating exercise, entertaining the patient is only a secondary consideration. The promotion of patient health is the primary consideration.

Furthermore, the game encourages physical activity that is medically vetted as being positive for patients, and as avoiding repetitive stress injuries. While the patient might engage in any type of physical activity while playing the game, the physical activity that will cause the most progress in game state are physical activities that have been vetted by clinicians to avoid repetitive stress injury. Furthermore, the game may provide instructions for performing the activity. Thus, healthy physical activity is encouraged. In some embodiments, the physical activity encourages full motion of a limb (e.g., an arm or leg) of the patient for between 5 and 10 minutes long.

When input is received (Yes in decision block 403) as a result of patient physical activity, the received input may be stored (act 405) by the patient computing system and/or by the clinician computing system in a manner that the input may be visualized to a clinician, for a clinician's assessment of the performance of the patient when performing the physical activity.

In addition, to encourage further physical activity, the patient computing system causes the game state to be changed (act 406) in response to the input ("Yes" in decision block 403) caused by the physical activity of the patient. The game state is caused to be changed dependent on the game parameters that are specific to the patient. Thus, the physical activity encouraged by the game may differ by patient. For instance, a child may be encouraged to move her arms more quickly to have the game react most positively, whereas for an older patient with arthritis in the right shoulder, slower and smoother motions may be encouraged when using the right arm, whereas moderately faster motions may be encouraged when using the left arm.

After the game responds to the game state (act 406), processing returns back to decision block 403 to await further input caused by patient physical activity. When patient physical activity is continuous, this process may be continually repeated such that the game state response in real-time and continuously to continuous activity by the patient.

The clinical computing system is communicatively coupled to the patient computing system so as to receive a representation of at least some of the input representing the physical activity of the patient. For instance, the clinical computing system may gather the input as it is stored in act 405 of the method 400 in response to each input received due to patient physical activity. Alternatively or in addition, the clinical computing system may periodically receive input from the patient as the patient is playing the game, with the input being stored at the patient computing system between transmissions to the clinical computing system. Alternatively or in addition, the clinical computing system may just receive the input once the patient has completed the game, with the input being stored at the patient computing system as it is accumulated during the game.

The clinical computing system further visualizes the received input to the clinician, so that the clinician can apply medical judgment in evaluating the performance of the patient during the game. For instance, the clinician might detect strengthening or improved range of motion of the patient. The clinician might evaluate the performance of the most recently played game with prior games, to detect trends in performance. The clinician computing system might also automatically detect significant trends, and display alerts to the clinician to potentially prompt further clinician evaluation.

The clinician computing system may use this same user interface to define game parameters for the patient, or provide clinician input from which game parameters are derived. The clinician may perhaps adjust the game parameters for the next game to be played by the patient. In one embodiment, the clinician might adjust game parameters mid-game, and the clinical computing system might respond by pushing the changed game parameters to the patient computing system for more immediate incorporation into the current game. In some embodiments in which the clinician computing system provides alerts to the clinician computing system, if the clinician computing system detects a potential danger to the patient (e.g., physical activity that deviates significantly from the encouraged activity that has been medically vetted), a more immediate alert may be given to the clinician, prompting the clinician to change the parameters mid-game, or perhaps contact or visit the patient to give verbal instructions and/or medical evaluation.

Patients that are undergoing disease therapy are responsive to positive encouragement. When the game itself involves visualizations that relate to coping with and/or overcoming the patient's disease, this often translates to the patient mentally visualizing coping with and/or overcoming the disease. This positive thinking leads to a better medical condition for the patient, and often an improved immune system.

To encourage positive thinking, the game may allow the patient to always win. While there may be different end game states, the patient is always provided with a mental reward upon completion of the game. For instance, perhaps a patient avatar is strengthened, or a game visualization representing the disease is weakened. Perhaps additional game characters participate as the game progresses to assist the patient avatar in overcoming the character representing the disease. This helps the patient remember or feel that there are people that care for him/her as the patient overcomes or copes with the disease.

The game may involve visualizations of tools that the patient may use to overcome a visualized character representing the disease. In some embodiments, there is no fighting within the game, and there is no use of violence against living things or weapons within the game. The tool may have a visualization of the drug they are taking to thereby help the patient know the connection between compliance with take prescription medicines, or other over the counter medicines, and an improved ability to overcome the disease. The game may involve visualized activities that address specific challenges associated with the patients' disease.

For instance, suppose a young female patient has cancer. In that case, the disease character might be a mountain that becomes smaller as the game progresses. The female patient might have a magic princess wand, that is associated with the chemotherapy drug being administered to the patient. The patient avatar might be a princess who is assisted by an ever growing throng of elves with shovels that help by digging away at the mountain, which becomes smaller and smaller.

As another example, suppose that a patient has clinical depression. The disease characters might be dark clouds that clear away or lighten as the game progresses. The patient avatar might be a wizard with the capability to emit sunshine from his fingertips. The sunshine might be labeled or somehow visually associated with the drug that the patient is taking for depression. As the clouds clear, perhaps loving images of the patient's loved ones become visible in the blue sky. Such loved ones might blow the remaining clouds away.

Thus, what is described is a disease therapy progress in which a clinician can customize the game for the patient, and which provides encouragement of vetted physical activity that is appropriate and customized for the patient. The patient further receives positive psychological messages as they progress through the game, helping the patient have a positive psychological outlook, which promotes healing.

Figure 5:
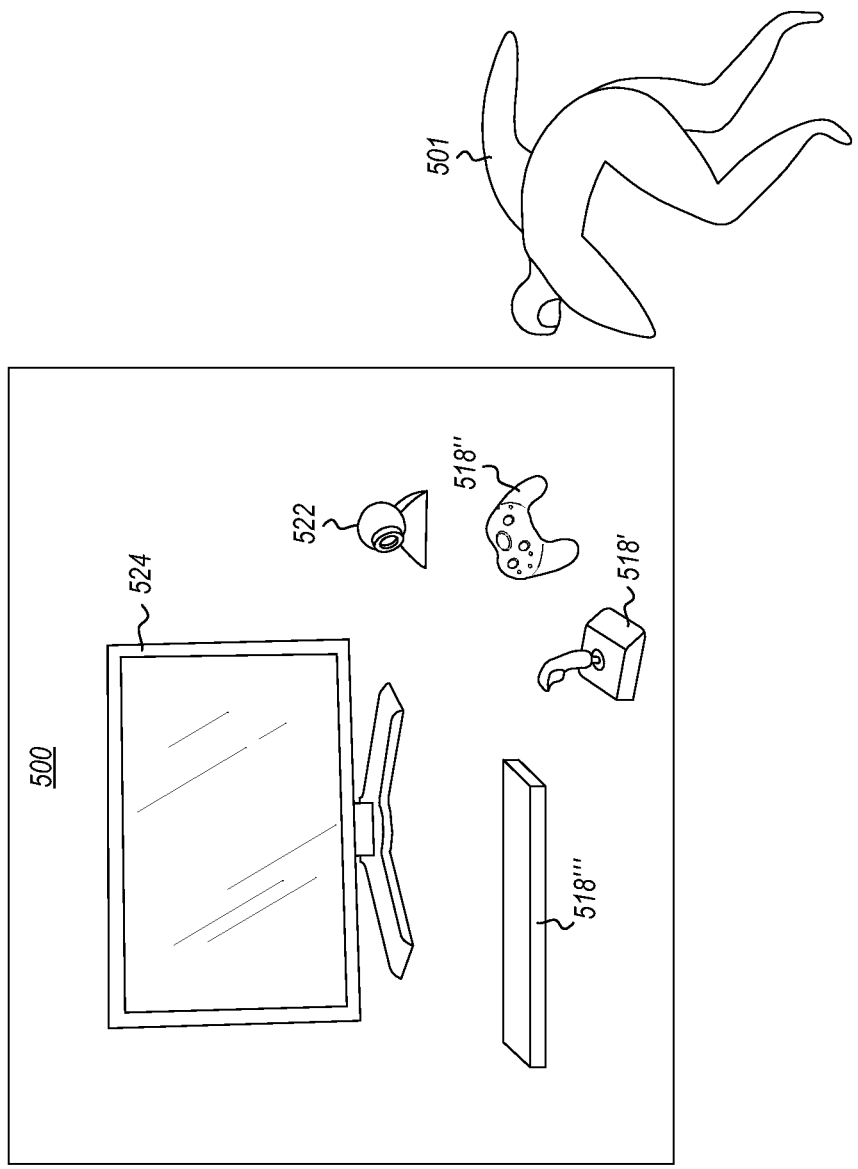
FIG. 5 illustrates a block diagram of a patient interaction with a disease therapy game system.

With reference to FIG. 5, a block diagram of a patient interaction with a patient computing system 320 (also referred to hereinafter as the "disease therapy game system" 500) of FIG. 3 is shown in accordance with an example embodiment. With reference to the example embodiment of FIG. 5, the patient computing system includes display 524, a joystick 518', a remote control 518", a balance board 518''', and motion sensor 522. Joystick 518', remote control 518", and balance board 518''' are examples game controls. A patient 501 may use joystick 518', remote control 518", and/or balance board 518''' to interact with disease therapy game application, which controls the presentation of content on display 524. For example, patient 501 may physically move joystick 518', remote control 518", and/or balance board 518''' as part of a physical activity requested to be performed by the patient as part of execution of disease therapy game application by disease therapy game system 500.

Additionally, components of a motion sensing system may be attached to the body of patient 501. Movement of a part of the body of patient 500 may be detected using motion sensor 522 and input to disease therapy game application to measure a response to the physical activity requested to be performed by the patient. For example, motion sensor 522 may be attached to a wrist and/or ankle of patient 501 or any other body part such as the head, torso, forearm, waist, neck, etc. For younger patients with compromised physical abilities, motion sensor 522 may be directly attached to the wrist and/or ankle. For other patients, wrist and/or ankle strap-on weights may be used. The weight of the strap-on weights used during the exercise may be determined by a clinician such as a physician, nurse, occupational therapist, physical therapist, or other healthcare professional. The components of the motion sensing system may be wireless or wired and detect movement in three dimensions including the acceleration and the velocity of the movement.

Figure 6:
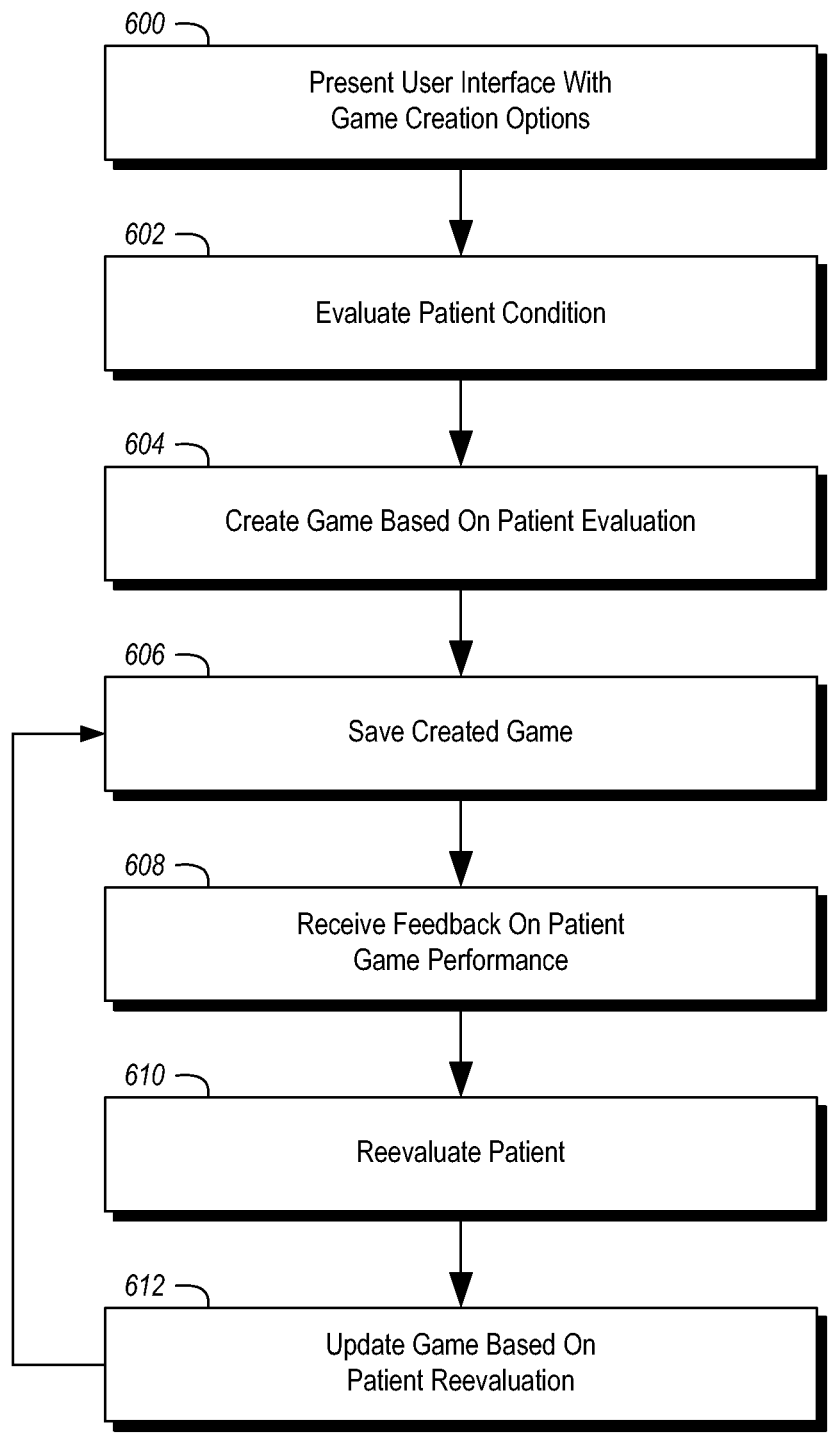
FIG. 6 illustrates example operations associated with the clinician computing system.

With reference to FIG. 6, example operations associated with clinician computing system is described. Additional, fewer, or different operations may be performed depending on the embodiment. The order of presentation of the operations of FIG. 6 is not intended to be limiting. A clinician can interact with one or more user interface windows presented to the clinician in display under control of a disease therapy game design application running on the clinician computing system independently or through use of a browser application. Thus, although some of the operational flows are presented in sequence, the various operations may be performed in various repetitions, concurrently, and/or in other orders than those that are illustrated.

The clinician may log into the disease therapy game design application as known to a person of skill in the art. For example, the clinician may execute the disease therapy game design application which causes presentation of a first user interface window, which may include a plurality of menus and selectors such as drop down menus, buttons, text boxes, hyperlinks, etc. associated with disease therapy game design application. In an illustrative embodiment, the clinician is a healthcare professional such as a physician, physician's assistant, nurse, nurse practitioner, occupational therapist, physical therapist, and so forth.

In an operation 600, the clinician may execute the disease therapy game design application which causes presentation of a user interface window that allows the clinician to select from among various game creation options. In an operation 602, the clinician evaluates a condition of the patient based on the patient's disease state, disease type, age, physical condition, and potentially other medically relevant characteristics. In an operation 604, the clinician creates a game for the patient based on the patient evaluation. For example, the clinician may be able to select the type, duration, range of motion, and order of performance of certain types of physical movements by the patient based on the patient's disease state, disease type, age, physical condition, and so forth. The clinician also may be able to select or define other characteristics of the game such as the game environment, the scoring/reward method, and so forth. Diseases may include, but are not limited to, neurodegenerative diseases, such as Alzheimer's diseases or Parkinson's disease, diabetes, a metabolic disease, an infectious disease, a neurological disease, cancer, cystic fibrosis, stroke, epilepsy, neuropathic pain, multiple sclerosis, etc.

In an operation 606, the clinician saves the created game. For example, the created game may be saved to database 340 for access by the patient at home using disease therapy game system 500. As another option, the created game may be saved to a computer readable medium for use by patient 501 in the clinician's medical facility. As yet another option, the created game may be saved to a computer readable medium such as a flash drive, CD, or DVD so that patient 501 can save the created game to computer readable medium of disease therapy game system 500.

In an operation 608, feedback is received relative to the patient's game performance. The feedback may be received minutes, days, weeks, months, and so forth after the created game is saved in operation 606. In an operation 610, the clinician reevaluates patient 501. For example, the clinician determines if the condition of patient 501 has improved, deteriorated, or remained the same. In an operation 612, the clinician updates the game based on the patient reevaluation and processing continues at operation 606, which saves the updated game.

With reference to FIG. 6, example operations associated with disease therapy game application are described. Additional, fewer, or different operations may be performed depending on the embodiment. The order of presentation of the operations of FIG. 6 is not intended to be limiting. Patient 501 can interact with one or more user interface windows presented to patient 501 in a display under control of disease therapy game application independently or through use of a browser application in an order selectable by patient 501. Thus, although some of the operational flows are presented in sequence, the various operations may be performed in various repetitions, concurrently, and/or in other orders than those that are illustrated.

Figure 7:
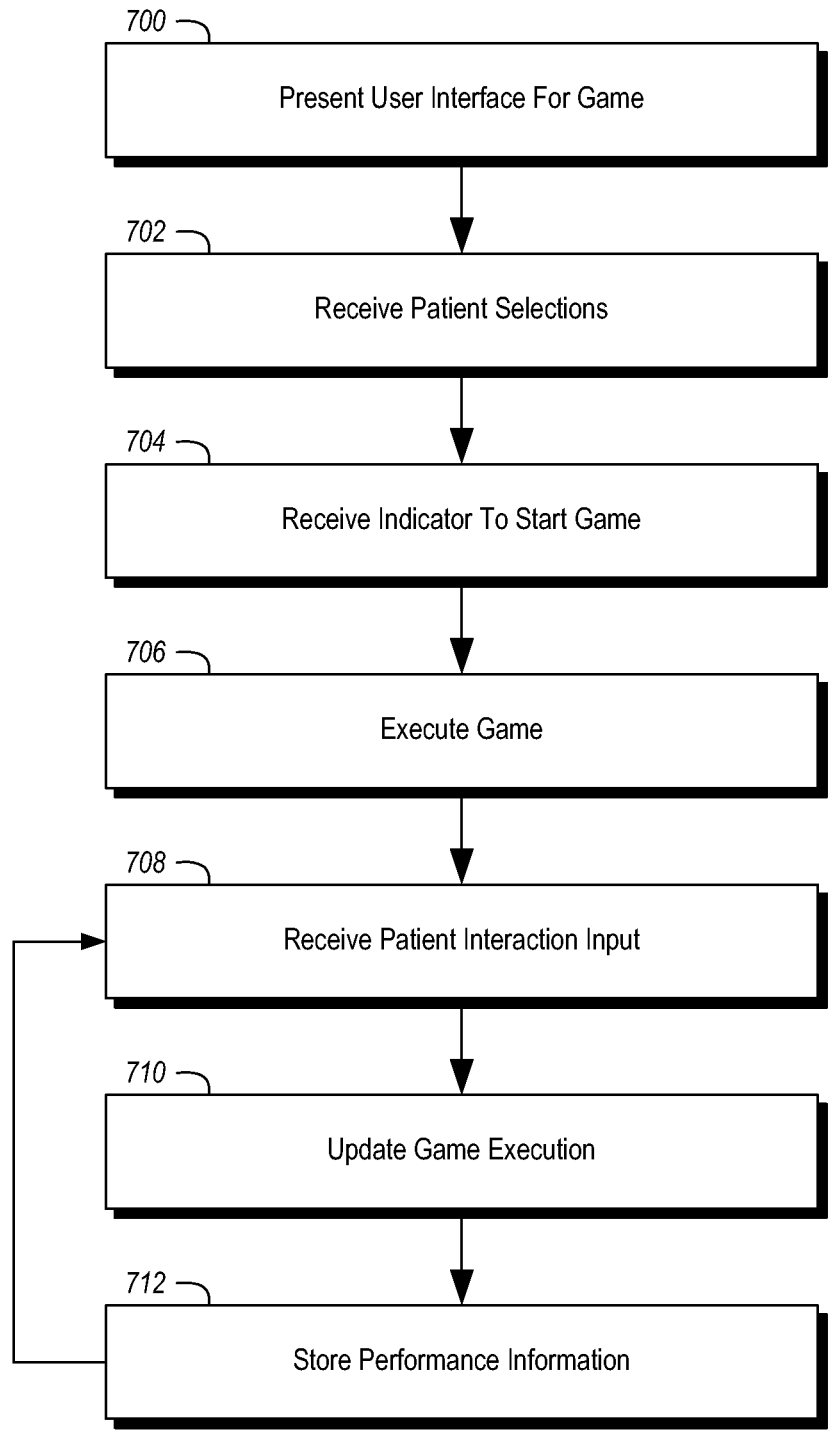
FIG. 7 illustrates example operations associated with a patient interfacing with the disease therapy game system.

FIG. 7 illustrates example operations associated with a patient interacting with the disease therapy system. The patient 501 may "login" to use disease therapy game application as known to a person of skill in the art. For example, patient 501 may execute disease therapy game application which causes presentation of a first user interface window, which may include a plurality of menus and selectors such as drop down menus, buttons, text boxes, hyperlinks, etc. associated with disease therapy game application.

In an operation 700, patient 501 may execute disease therapy game application 112, which causes presentation of a user interface window that allows patient 501 to select from among various game creation options. For example, patient 501 may be able to select an avatar to represent patient 501 in a display during execution of disease therapy game application. For example, patient 501 may select the avatar based upon a healthy version of himself or a character he participates in creating so that patient 501 identifies with the avatar either through likeness, investment, or identification with an archetype. Patient 501 further may select an avatar sidekick that is created, for example, based on a patient's favorite toy companion such as a stuffed animal, LEGO® model, favorite blanket, and so forth.

The following table lists a non-inclusive list of various diseases, possible corresponding disease avatars, and corresponding possible patient avatars that might be selected in a disease therapy game associated with the disease.

TABLE 1

| Disease | Disease avatar | Patient avatar |
|---|---|---|
| Cancer | Alien representing a cancer cell | Superman/Superwoman |
| Cancer | A bug representing a cancer cell | Fairy/Wizard |
| Cystic Fibrosis | A monster representing a cystic fibrosis cell | Spiderman/Wonderwoman |
| Epilepsy | Thunderstorms representing hyperexcitable neurons | Super-hero |
| Alzheimer disease | Weeds representing amyloid plaques | Gardener |
| Diabetes | Buzzing flies representing excess of blood sugar | Terminator |

However, the patient avatar may be selected from a wide variety of possible selections so as to choose an avatar with which the patient would most like to be associated.

With continuing reference to FIG. 7, in an operation 702, the patient selections are received. In an operation 704, an indicator indicating a start of execution of the game is received. In an operation 706, execution of the game is initiated based on the characteristics defined/selected by the clinician and patient 501. In an operation 708, a patient interaction input is received. For example, the motion sensor 522 detects a movement of the body of patient 501 in response to the game execution. During execution, disease therapy game application presents a visualization of patient 501 fighting the disease suffered by patient 501.

An opponent as selected by the clinician or patient 501 may be represented by a personally designed avatar in the form of a disease cell, a monster, or an alien. For each movement of the hands and/or legs of patient 501, the opponent may shrink until the opponent completely disappears. An exercise game session may target fighting several opponents. Using the disease therapy game application, any physical exercise including breathing may be coupled to a movement of a symbol that reflects fighting the disease.

In an operation 710, the game execution is updated. For example, the game initiates execution of a new exercise or body movement or portion of the game or provides a reward to patient based on the performance of the movement by patient. In an operation 712, performance information related to the movement by patient 501 is stored as previously mentioned.

Other examples of incentive-based devices include any type of exercise equipment, such as a stationary bike, elliptical, or rowing machine, that directly couples physical movements to visualization of fighting a disease. For example, an electronic display may show that each physical movement "fuels" a rocket that attacks a symbol of a disease instead of the calories burned.

Embodiments described herein comprise testing of the game in clinical trials for its efficacy as adjuvant therapy. Efficacy with respect to improving exercise stamina is assessed by measuring physiological and cardiovascular parameters. Efficacy with respect to empowerment/resilience is assessed using existing validated questionnaire tools including the Child Health Questionnaire, the Rosenberg Self Esteem Scale and the Borg Scale of Perceived Exertion.

The principles described herein allow a patient to directly administer his/her "adjuvant empowerment therapy" tailored to his/her specific disease along with appropriate pharmacological treatments. At least one embodiment described herein relates to a method for bridging physical exercise and mental empowerment via positive visualization. At least one embodiment described herein relates to a method for providing diverse physical exercises that accompany stories and positive visualization using metaphors for fighting cancer or other diseases.

Figure 8:
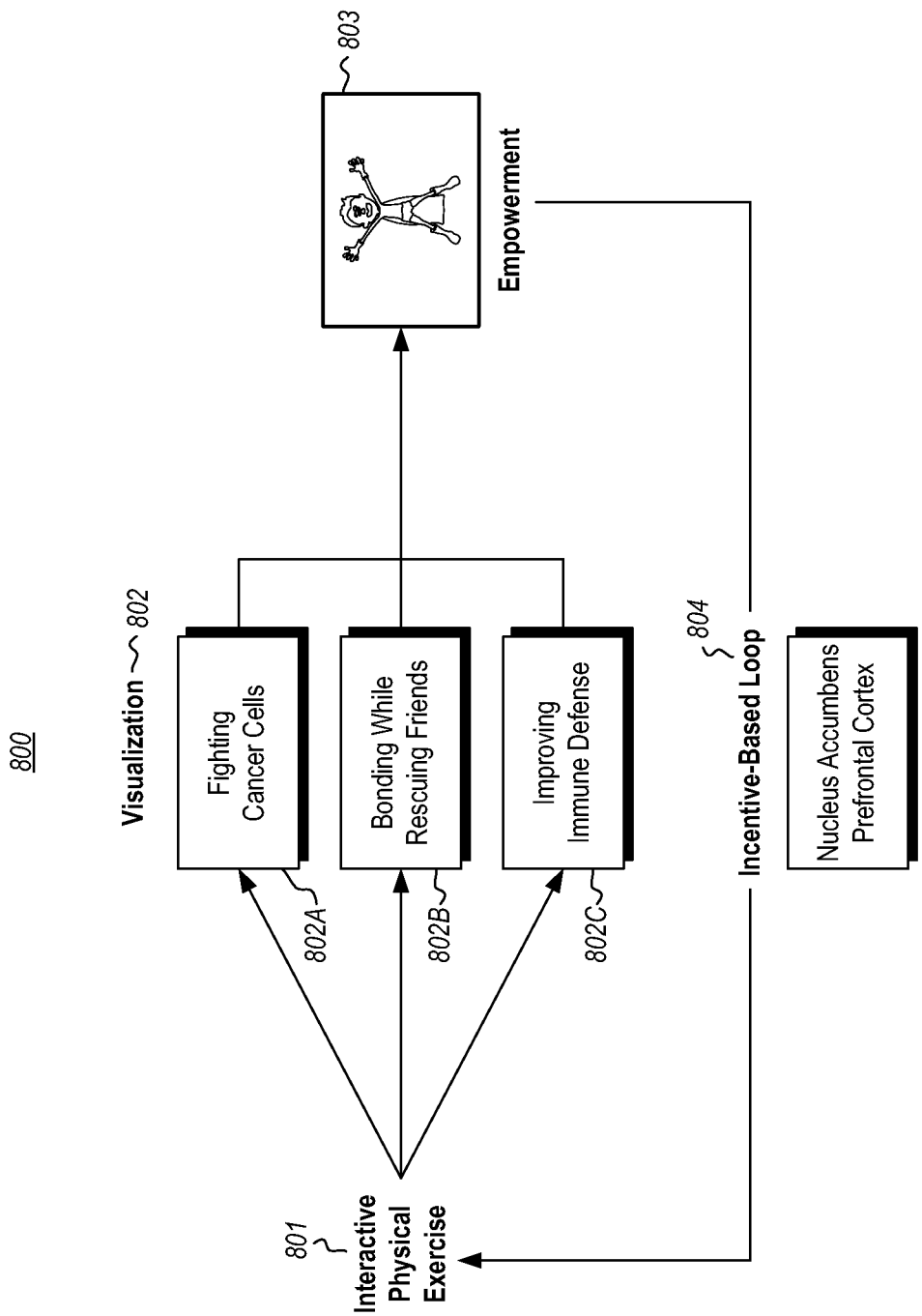
FIG. 8 illustrates an example of interactions between a patient and a disease therapy game system.

For instance, in FIG. 8, which illustrates interactions between a patient and a disease therapy system as described herein, the patient engages in interactive physical exercise 801. This leads to the game visualizing to the patient empowering visualizations 802 such as, for example, visualizations 802A suggesting the fighting of cancer cells, visualizations 802B of bonding while rescuing friends, visualizations 802C of improving the immune system, and so forth. This results in patient empowerment 803 through empowering brain activity 804, such as healing stimulations of the nucleus accumbens and prefrontal cortex.

Thus, the disease therapy game promotes physical activity and stamina, fighting spirit and teamwork, and a sense of well-being and personal empowerment during treatment of a disease. Players, represented by friendly characters, engage in self-empowering contests on screen, either alone or in cooperation with others (physicians, nurses, caregivers, family and friends) against the robotic, disease-related "foe"

avatar that is disease-specific. Visual and audio responses provide immediate feedback and positive reinforcement.

Figure 9:
FIG. 9 illustrates an example of using a disease therapy game system by a patient in a hospital.

At least one embodiment described herein relates to a method for helping a patient to overcome a disease by physical exercise and empowerment, as illustrated in 9. In the case of FIG. 9, a support person 901 engages with the game 902 along with the patient 903.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system for providing a virtual disease therapy environment for a patient, comprising:
    a patient computing system comprising:
        one or more processors; and
        one or more storage devices having stored thereon computer-executable instructions that are executable by the one or more processors, and that configure the patient computing system to create a clinician-customized virtual disease therapy environment, including computer-executable instructions that configure the computer system to perform at least the following:
            execute a game in response to a request,
            accessing from a remote computer database game parameters that are associated with a patient, wherein the game parameters were created due to action of a remote clinician as part of a disease therapy program,
            execute the game when requested such that when the game is executed, the game is executed using the identified game parameters associated with the patient,
            receive heart-rate readings from a heart-rate sensor representing physical activity of the patient, wherein the heart-rate readings are generated by one or more electronic heart-rate sensors that monitor physical attributes of the patient, and
            change game state dependent on the game parameters and the heart-rate readings such that the patient's heart-rate remains within an ideal range, wherein the game involves at least one entity that represents a disease, and that the entity becomes weaker or diminishing as a direct result of the patient's physical activity, and
            activate a cool down timer when the heart-rate readings indicate that a heart-rate of the patient has exceeded a pre-determined rate, wherein once the cool down timer is activated, the patient cannot engage in identical physical activity until the cool down timer expires; and
    a clinician computing system comprising:
        one or more processors; and
        one or more storage devices having stored thereon computer-executable instructions that are executable by the one or more processors, and that configure the clinician computing system to create a clinician-customized virtual disease therapy environment, including computer-executable instructions that configure the computer system to perform at least the following:
            communicatively couple to the patient computing system so as to receive a representation of at least some of the heart-rate sensor readings representing the physical activity of the patient, and configured to cause the representation to be visualized to a clinician; and
    the one or more electronic sensors configured to monitor physical activity of the patient, wherein the one or more sensors comprise the heart-rate sensor.

2. The system in accordance with claim 1, wherein the clinician computing system receives at least some of the sensor readings representing physical activity by accessing a store that the patient computing system writes the sensor readings to.

3. The system in accordance with claim 1, wherein the clinician computing system is remotely accessible to the clinician to allow the game parameters to change.

4. The system in accordance with claim 1, wherein the clinical computing system further comprises a user interface that a clinician may use to cause the identified game parameters to be created and associated with the patient.

5. The system in accordance with claim 1, wherein the clinical computing system further comprises a user interface that a clinician may use to cause the identified game parameters to be altered, thereby causing a change in effect of physical activity of the patient on game state.

6. The system in accordance with claim 1, wherein the physical activity comprises full motion of at least a limb of the patient, which comprises exercise that is between 5 and 10 minutes long.

7. The system in accordance with claim 1, wherein the physical activity movements are visualized by the game as activities that relate to coping with or/and overcoming the patient's disease.

8. The system in accordance with claim 1, wherein at least one of the game parameters is defined by a computing module in response to clinician input.

9. The system in accordance with claim 1, wherein at least one of the game parameters is defined by a computing module in response to dynamically changing conditions measured by the computing module.

10. The system in accordance with claim 1, wherein at least one of the game parameters is defined by a computing module in response to patient compliance.

11. The system in accordance with claim 1, wherein at least one of the game parameters is directly defined by a clinician.

12. The system in accordance with claim 1, wherein physical activity that will cause the most progress in game state are physical activities that have been vetted by clinicians to avoid repetitive stress injury.

13. The system in accordance with claim 1, wherein the game includes a cool down timer that is activated when the sensor readings indicate that the physical activity of the patient has reached a pre-determined time duration of the physical activity, wherein once the cool down timer is activated, the patient cannot engage in identical physical activity until the cool down timer expires.

14. The system in accordance with claim 1, wherein all end game states of the game result in a reward for the patient.

15. The system in accordance with claim 1, wherein the game involves a plurality of characters that are assisting the patient.

16. The system in accordance with claim 1, wherein the game involves a tool that may be used to fight the entities, the tool represents a drug that the patient is taking.

17. The system in accordance with claim 16, wherein the tool is labeled with a name of the drug that the tool represents.

18. The system in accordance with claim 1, wherein the game involves overcoming a disease of the disease therapy program without using violence or weapons.

19. The system in accordance with claim 1, wherein the game involves visualized activities that address specific challenges and characteristics of a disease of the disease therapy program.

20. The system in accordance with claim 1, wherein the game involves an avatar that is associated with the patient, and that becomes stronger as the game progresses.

21. A computer implemented method for disease therapy comprising:
   receiving, by a patient computing system, an indicator to start execution of a game;
   receiving from a remote computer database game parameters, wherein the game parameters include an ideal heart rate associated with the patient and created due to action by a remote clinician as part of a disease therapy program;
   executing the game with the identified game parameters by the patient computing system, wherein the game requires a physical activity by a patient;
   receiving, from one or more heart-rate sensors, heart-rate readings related to the physical activity of the patient in response to execution of the game, wherein the one or more heart-rate sensors measure physical attributes of the patient;
   activating a cool down timer when the heart-rate sensor readings indicate that the heart-rate of the patient has exceeded a pre-determined rate, wherein once the cool down timer is activated, the patient cannot engage in identical physical activity until the cool down timer expires, and
   storing the heart-rate readings for assessment of the performance of the patient when performing the physical activity.

22. A method of using the system in accordance with claim 21, as adjunct therapy to treat neurological and mental disorders.

23. A computer program product comprising one or more non-transitory computer storage media having thereon one or more computer-executable instructions that are executable by one or more processors of a patient computing system to perform the following:
   initiating a game;
   accessing, from a remote computer database, game parameters that comprise an ideal range of motion of a particular limb of a patient and that are created due to action by a remote clinician as part of a disease therapy program;
   executing the game with the identified game parameters,
   receiving sensor readings, from one or more motion sensors, indicating physical activity by a patient, wherein the one or more motion sensors measure a range of motion of the particular limb of the patient;
   progressing game state dependent on the measured range of motion and dependent on the identified game parameters, wherein the game involves an avatar that is associated with the patient, and that becomes stronger as the game progresses;
   activating a cool down timer when heart-rate sensor readings indicate that the heart-rate of the patient has exceeded a pre-determined rate, wherein once the cool down timer is activated, the patient cannot engage in identical physical activity until the cool down timer expires, and
   causing a representation of at least a portion of the received sensor readings to be stored for assessment of the performance of the patient when performing the physical activity.

24. The computer program product comprising one or more non-transitory computer storage media in accordance with claim 23, wherein the progressing of the game state occurs repeatedly in response to sensor readings representing physical activity of the patient.

* * * * *